United States Patent [19]

Pettit et al.

[11] Patent Number: 5,530,097
[45] Date of Patent: Jun. 25, 1996

[54] HUMAN CANCER INHIBITORY PEPTIDE AMIDES

[75] Inventors: George R. Pettit, Paradise Valley; Jayaram K. Srirangam, Tempe; Michael D. Williams, Mesa, all of Ariz.

[73] Assignee: Arizona Board of Regents acting on behalf of Arizona State University, Tempe, Ariz.

[21] Appl. No.: 283,684

[22] Filed: Aug. 1, 1994

[51] Int. Cl.$^6$ .............................. A61K 38/04; C07K 5/00
[52] U.S. Cl. ................. 530/330; 530/331; 530/321
[58] Field of Search ............................. 530/321, 330, 530/331; 514/18

[56]  References Cited

U.S. PATENT DOCUMENTS

| | | | |
|---|---|---|---|
| 4,816,444 | 3/1989 | Pettit | 514/17 |
| 5,017,691 | 5/1991 | Lee | 535/351 |
| 5,410,024 | 4/1995 | Pettit et al. | 530/330 |

FOREIGN PATENT DOCUMENTS 600744  6/1994  European Pat. Off. .

*Primary Examiner*—Christine M. Nucker
*Assistant Examiner*—Benet Prickril

*Attorney, Agent, or Firm*—Richard R. Mybeck; Walter R. Mybect II

[57]  ABSTRACT

This application discloses seven newly synthesized pentapeptide amides and four tetrapeptide amides. The synthesis utilized both naturally occurring and modified amino acids; the modified amino acids are constituents of the well known dolastatin 10 and dolastatin 15 which are structurally distinct peptides with excellent antineoplastic activity. These peptides were constructed by introducing a peptide bond between selected amino acids and modified amino acids and coupling the resulting di- and tri-peptides to obtain peptides having a high anticancer activity against a series of human cancer cell lines.

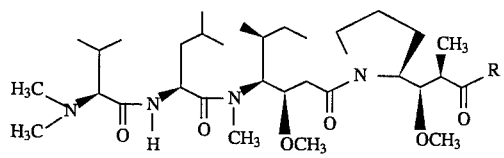

8a) R = Met—NH—2ClPh
8b) R = Met—NH—4ClPh
8c) R = Phe—NH—3ClPh
8d) R = Phe—NH—4ClPh
8e) R = Met—NH—BnThz
8f) R = Pro—NH—BnThz
8g) R = Met—NH—Q

8 Claims, No Drawings

5,530,097

HUMAN CANCER INHIBITORY PEPTIDE AMIDES

Financial assistance for this project was provided by U.S. Government Grant Number OIG-CA44344-01-04-05; and the United States Government may own certain rights to this invention.

INTRODUCTION

This invention relates generally to the field of cancer chemotherapy and more particularly to the synthesis of unique pentapeptide amides and tetrapeptide amide derivatives of dolastatin 10 which may be useful in chemotherapy.

BACKGROUND OF THE INVENTION

Ancient marine invertebrate species of the *Phyla Bryozoa, Molluska,* and *Porifera* have been well established in the oceans for over one billion years. Such organisms have undergone trillions of biosynthetic reactions of their evolutionary chemistry to reach their present level of cellular organization, regulation and defense.

For example, marine sponges have changed minimally in physical appearance for nearly 500 million years. This suggests a very effective chemical resistance to evolution in response to changing environmental conditions over that period of time. Recognition of the potential for utilizing this biologically potent marine animal for medicinal purposes was recorded in Egypt about 2,700 B.C. and by 200 B.C. certain sea hare extracts were being used in Greece for their curative affect. This consideration along with the observation that marine animals, e.g. invertebrates and sharks, rarely develop cancer led to the systematic investigation of marine animal and plant anticancer compounds.

By 1968, ample evidence had been obtained, based on the U.S. National Cancer Institute's (NCI) key experimental cancer study systems, that certain marine organisms could provide new and antineoplastic and/or cytotoxic agents useful in chemotherapy and might also lead to compounds which would be effective in the control and/or eradication of viral diseases.

Further, these marine organisms were believed to possess potentially useful drug candidates of unprecedented structure which had eluded discovery by other methods of medicinal chemistry. Fortunately, these expectations have been realized, e.g. the discovery of the bryostatins, dolastatins and cephalostatins, many of which are now in preclinical development or human clinical studies.

Those researchers presently involved in medicinal chemistry know well the time lag between the isolation of a new compound and its introduction to the market. Often this procedure takes several years and may take decades. As a result, industry, in association with the U.S. Government, has developed a system of testing criteria which serves two purposes. One is to eliminate those substances which are shown through testing to be economically counterproductive to pursue. The second, more important purpose serves to identify those compounds which demonstrate a high likelihood of success and therefore warrant the further study and qualification, and attendant expense, necessary to meet the stringent regulatory requirements which control the ultimate market place.

The current cost to develop the necessary data required for lawful marketing of a new drug compound approaches ten million dollars per compound. Economics dictate that such a huge investment be made only when there is a reasonable likelihood that it can be recovered. Absent such a likelihood, there will be no investment and, without investment, the research requisite for the discovery of these potentially life saving compounds will cease.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and is accepted in scientific circles. The protocol, and the established statistical means for analyzing the results obtained by the standardized testing are fully described in the literature. See: Boyd, Dr. Michael R., *Principles & Practice of Oncology,* PPO Updates, Volume 3, Number 10, October 1989, for an in depth description of the testing protocol; and Paull, K. D., "Display and Analysis of Patterns of Differential Activity of Drugs Against Human Tumor Cell Lines; Development of Mean Graph and COMPARE Algorithm", *Journal of the National Cancer Institute Reports,* Vol. 81, No. 14, Page 1088, July 14, 1989 for a description of the methods of statistical analysis. Both of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures possessing antineoplastic qualities. The collection and processing of these later compounds from their natural sources ranges from grossly impractical to the utterly impossible. Ignoring the ecological impact, the population of these creatures and the cost of collection and extraction make the process unworkable. Artificial synthesis of the active compounds is the only possible solution.

Therefore, the elucidation of the structure of these antineoplastic compounds is essential. After the structure has been determined, then a means of synthesis must be determined. This is often a long and arduous procedure due to the idiosyncratic complexity of these naturally occurring, evolutionary modified compounds. In addition, research is necessary to determine whether any portion of the naturally occurring compound is irrelevant to the desired properties, so that focus can be on the simplest structure having the perceived properties.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The inhibition of human cancerous tumor growth as evidenced by NCI cell line data is utilitarian in that it relieves these conditions, thereby allowing the human thus afflicted to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive and the means for further research.

The recognition of antineoplastic and tumor inhibiting activity as demonstrated by accepted NCI criteria as "utility" can promote research efforts in the United States and is unequivocally essential if those efforts are to obtain even a modest modicum of success. To reject the NCI criteria on any grounds can only result in quashing all further efforts in the United States and leave our people at the mercy of those foreign companies who operate in more foresighted jurisdictions.

BRIEF SUMMARY OF THE INVENTION

The investigation of potentially useful antineoplastic peptides offers one of the most promising approaches to new anticancer drugs. Continuing research along these lines has now resulted in the discovery and synthesis of seven new pentapeptide amides and four new tetrapeptide amides. In the syntheses of these peptides, naturally occurring as well as some modified amino acids have been utilized. The modified amino acids disclosed herein are constituents of the well known dolastatin 10 and dolastatin 15 which are structurally distinct peptides with excellent antineoplastic activity. Presently dolastatin 10 represents the most important member of the dolastatin family and is a potentially useful anticancer drug. Herein disclosed are new compounds having excellent activity against a series of human cancer cell lines.

The novel peptides disclosed herein were constructed by introduction of a peptide bond between selected amino acids and modified amino acids and coupling the resulting di- and tripeptides to obtain peptides having a very high anticancer activity. The research has led to the discovery and synthesis of new and very potent anticancer peptide amides. The present disclosure involves eleven such compounds: namely seven pentapeptide amides herein designated 8a–g and four tetrapeptide amides herein designated 10a–d.

The synthesis of these compounds was achieved in the following manner using the following terminology and abbreviations: the abbreviations are as follows:

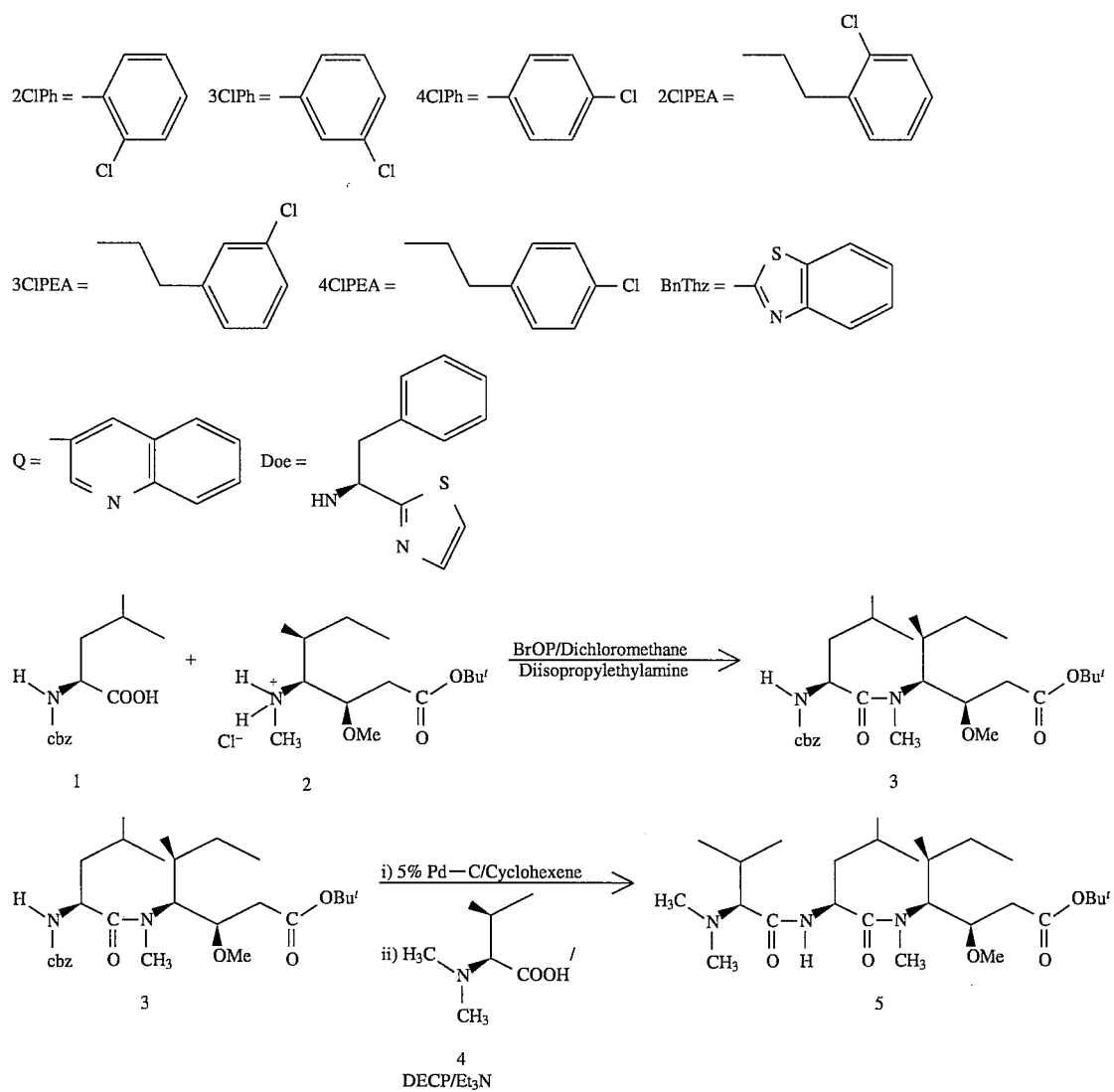

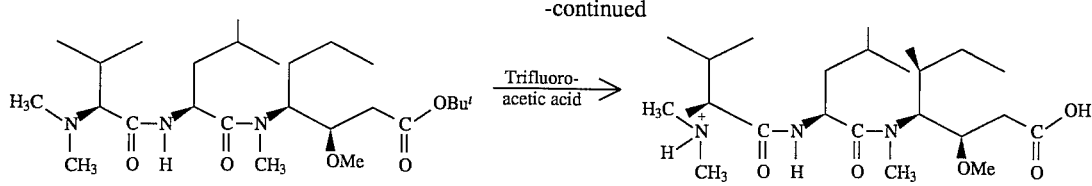

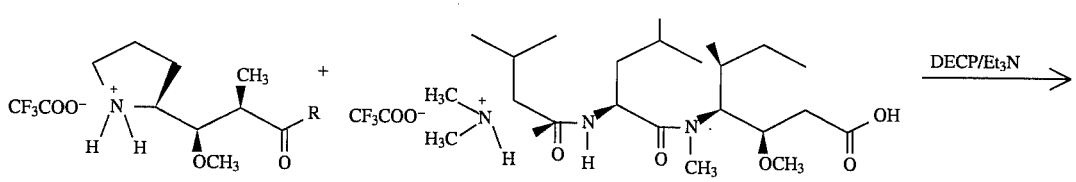

| 7a) | R = Met—NH—2ClPh | 7g) | R = Met—NH—Q |
| --- | --- | --- | --- |
| 7b) | R = Met—NH—4ClPh | 9a) | R = Doe |
| 7c) | R = Phe—NH—3ClPh | 9b) | R = NH—2ClPEA |
| 7d) | R = Phe—NH—4ClPh | 9c) | R = NH—3ClPEA |
| 7e) | R = Met—NH—BnThz | 9d) | R = NH—4ClPEA |
| 7f) | R = Pro—NH—BnThz | | |

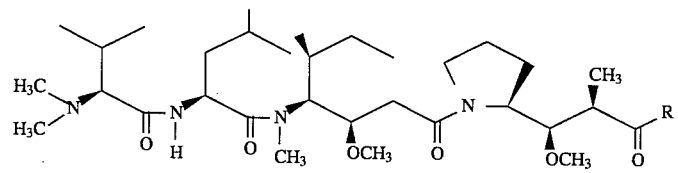

| 8a) | R = Met—NH—2ClPh | 8g) | R = Met—NH—Q |
| --- | --- | --- | --- |
| 8b) | R = Met—NH—4ClPh | 10a) | R = Doe |
| 8c) | R = Phe—NH—3ClPh | 10b) | R = NH—2ClPEA |
| 8d) | R = Phe—NH—4ClPh | 10c) | R = NH—3ClPEA |
| 8e) | R = Met—NH—BnThz | 10d) | R = NH—4ClPEA |
| 8f) | R = Pro—NH—BnThz | | |

The common tripeptide 5 needed for the synthesis of these peptides was synthesized starting from dolaisoleuine (Dil), a modified amino acid. Dolaisoleuine was coupled with N-cbz-(L)-Leucine (1) using bromotris (dimethylamino) phosphonium hexafluorophosphate (BrOP) as the coupling agent in presence of diisopropylethylamine to obtain the dipeptide N—Z—Leu—Dil—OBu$^t$ (3). The N-carbobenzyloxy protecting group of the dipeptide 3 was then removed with 5% Pd-C in cyclohexene to afford the free base which was coupled with dolavaline (Dov, a modified amino acid) with diethyl cyanophosphonate (DECP) as the coupling agent to give the required tripeptide Dov—Leu—Dil—OBu$^t$ (5). The t-boc protecting group of the tripeptide (5) was then removed with trifluoroacetic acid to obtain the trifluoroacetate salt (6).

The resulting tripeptide-tfa salt (6) was coupled with seven known dipeptide amide trifluoroacetate salts (7a–g) as well as four known dolaproine amide trifluoroacetate salts (9a–d) using DECP as the coupling agent to obtain the respective pentapeptide amides (8a–g) and tetrapeptide amides (10a–d) in good yields.

All these compounds demonstrated excellent growth inhibition when administered to a variety of human cancer and mouse leukemia cell lines. The biological results are disclosed in Tables 1 and 2 below.

Accordingly, the primary object of the subject invention is the synthesis of peptide derivatives of dolastatin 10, which demonstrates extraordinary inhibition of cell growth and/or anticancer activity at substantially reduced cost.

Another object of the present invention is to identify the active portions of dolastatin 10 derivatives which can be attached to other molecules to provide an equally effective but considerably less expensive tumor inhibiting agents.

These and still further objects as shall hereinafter appear are readily fulfilled by the present invention in a remarkably unexpected manner as will be readily discerned from the following detailed description of exemplary embodiments thereof.

DESCRIPTION OF THE PREFERRED EMBODIMENT

In vitro testing is an absolutely essential factor in the ongoing venture to discover new compounds for use in fighting the scourge of cancer. Without such screening, the process of obtaining new candidate drugs would be even more complex and expensive, if not impossible. To understand this process, and recognize the outstanding results demonstrated by some of the compositions disclosed herein, one must first understand the procedures, the nomenclature, and the data analysis involved. A brief description of the appropriate terminology follows:

$ED_{50}$ (P388) and $GI_{50}$ (HTCL) identify the drug dose which reduces the percent tumor/cell growth to 50%. There is no mathematical difference between $ED_{50}$ and $GI_{50}$, both of which are calculated using the same formula. The only difference is historical usage.

TGI, means "Total Growth Inhibition", and identifies the drug dose needed to yield zero percent growth, i.e. there are just as many cells at the end of the experiment as were present at the beginning. Whether just as many cells were killed as were produced (steady state), or no growth occurred (total inhibition) cannot be distinguished.

$LC_{50}$, means "Lethal Concentration 50%", and identifies the drug concentration which reduces to one-half of the cells originally present at the beginning of the experiment.

Each drug is tested at five (5) doses: 100—10–1–0.1—0.01 μg/mL. Percent Growths are calculated for each dose. The two (or three) doses with growth values above, below, (or near to) 50% growth are used to calculate the $ED_{50}/GI_{50}$ values using a linear regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at −50% growth for the $LC_{50}$.

At the start of each experiment, cells from the in vitro cell cultures are inoculated into the appropriate tubes or microtiter plates. One set of control tubes/plates is immediately counted to determine the number of cells at the start of the experiment. This is the "baseline count", or "Tzero reading". At the end of the experiment (48 hrs later), a second set of control tubes/plates is analyzed to determine the "Control Growth" value. The growth (or death) of cells relative to the initial quantity of cells is used to define the "Percent of Growth."

The synthesis of potentially useful peptides presents one of the most essential and promising approaches to new types of anticancer and immunosuppressant drugs. The Dolastatins, an unprecedented series of linear and cyclic antineoplastic and/or cytostatic peptides isolated from Indian Ocean sea hare *Dolabella auricularia* represent excellent leads for synthetic modification. The very productive sea hare *Dolabella auricularia* has produced a number of structurally distinct peptides with excellent antineoplastic activity. Presently Dolastatin 10, a linear pentapeptide, represents the most important member and is a potentially useful antineoplastic agent. Dolastatin 10 shows one of the best antineoplastic activity profiles against various cancer screens presently known. Recently the total synthesis and absolute configuration of this structurally unique and biologically active peptide was discovered. This compound has been tested in vivo and demonstrated significant activity, as shown below.

| Experimental Anticancer Activity of Dolastatin 10 in Murine in vivo Systems, T/C (μg/kg) | |
|---|---|
| P388 Lymphocytic Leukemia | B16 Melanoma |
| toxic (13.0) | 238 and 40% cures (11.11) |
| 155 and 17% cures (6.5) | 182 (6.67) |
| 146 and 17% cures (3.25) | 205 (4.0) |
| 137 (1.63) | 171 (3.4) |
| L1210 Lymphocytic Leukemia | 142 (1.44) |
| 152 (13) | M5076 Ovary Sarcoma |
| 135 (6.5) | toxic (26) |
| 139 (3.25) | 166 (13) |
| 120 (1.63) | 142 (6.5) |
| Human Mammary Xenograph | 151 (3.25) |
| Nude Mouse | LOX Human Melanoma Xenograph |
| Toxic (26) | (Nude Mouse) |
| 137 (13) | toxic (52) |
| 178 (6.25) | 301 and 67% cures (26) |
| OVCAR-3 Human Ovary Xenograph | 301 and 50% cures (13) |
| Nude Mouse | 206 and 33% cures (6.5) |
| 300 (40) | 170 and 17% cures (3.25) |
| MX-1 Human Mammary Xenograft | LOX in separate experiments |
| (Tumor Regression) | 340 and 50% cures (43) |
| 14 (52) | 181 and 33% cures (26) |
| 50 (26) | 192 (15) |
| 61 (13) | 138 and 17% cures (9.0) |
| 69 (6.25) | |

| | EXAMPLE: Baseline Count 20 Control Count 200 (10-Fold Growth) |
|---|---|
| 100% Growth = Control Growth | 100% Growth = 200 |
| 50% Growth = Tzero + $\frac{Control - Tzero}{2}$ | 50% Growth = 110 |
| 0% Growth = Tzero | 0% Growth = 20 |
| −50% Growth = Tzero/2 | −50% Growth = 10 |

Now that the relevant definitions and data analysis techniques have been disclosed, this disclosure can now turn to the particular compounds disclosed herein.

Dolastatin 10 has also been tested against a minipanel from the NCI Primary screen. These results appear below, showing the amount of Dolastatin 10 required to attain $GI_{50}$ in μg/ml, against the cell lines set forth below.

$$\frac{OVCAR-3}{9.5 \times 10^{-7}} \text{ (A)} \quad \frac{SF\ 295}{7.6 \times 10^{-8}} \text{ (B)} \quad \frac{A498}{2.6 \times 10^{-5}} \text{ (C)}$$

$$\frac{NCI-H460}{3.4 \times 10^{-6}} \text{ (D)} \quad \frac{KM2OL2}{4.7 \times 10^{-6}} \text{ (E)} \quad \frac{SK-MEL-5}{7.4 \times 10^{-6}} \text{ (F)}$$

Similarly, the compounds disclosed herein have also been tested against an NCI in vitro mini panel. For each of six cell lines $GI_{50}$, TGI, and $LC_{50}$ amounts were calculated for each compound. Each compound was also tested against the PS-388 cell line and for this test an $ED_{50}$ was calculated.

The protocols followed, for the NCI minipanel are, except for the number of cell lines, those established by M. R. Boyd Ph.D., and well known to those of ordinary skill in the art. The procedure followed for the test against PS-388 Leukemia is the same that was followed in the superseded NCI P-388 screening test, which is also well known to those having ordinary skill in the art.

residue was chromatographed on a SILICA GEL column using 1:4 acetone-hexane as the solvent to obtain the required dipeptide as an oily substance (3, 72%); $R_f$ 0.53 (1:4 acetone-hexane); $[\alpha]_D^{25}$ −33.4° (c 6.2, $CH_3OH$); IR(neat): 2961, 1723, 1640, 1528, 1456, 1368, 1254, 1154

TABLE 1

Human Cancer-Cell line and PS-388 Mouse Leukemia ($ED_{50}$) data for the pentapeptide amides 8a–g

| | Cell type | Cell line | 8 a | 8 b | 8 c | 8 d | 8 e | 8 f | 8 g |
|---|---|---|---|---|---|---|---|---|---|
| GI-50 (μg/ml) | Ovarian | OVCAR-3 | 0.00047 | 0.000031 | 0.000064 | 0.0000085 | 0.00008 | 0.0033 | <0.000006 |
| | CNS | SF-295 | 0.0034 | 0.0029 | 0.00088 | 0.00034 | 0.0036 | >0.01 | 0.00041 |
| | Renal | A498 | 0.0037 | 0.00045 | 0.00042 | 0.00018 | 0.00087 | >0.01 | 0.00026 |
| | Lung-NSC | NCI-H460 | 0.0028 | 0.003 | 0.0017 | 0.00032 | 0.0032 | >0.01 | 0.00032 |
| | Colon | KM20L2 | 0.0018 | 0.00028 | 0.00021 | 0.000015 | 0.00034 | 0.0074 | 0.000019 |
| | Melanoma | SK-MEL-5 | 0.042 | 0.000018 | 0.000042 | 0.0000051 | 0.000051 | 0.0043 | <0.000006 |
| TGI (μg/ml) | Ovarian | OVCAR-3 | 0.005 | 0.0016 | 0.0011 | 0.00023 | 0.0029 | >0.01 | 0.001 |
| | CNS | SF-295 | >0.01 | >0.01 | >0.01 | >0.01 | >0.01 | >0.01 | >0.01 |
| | Renal | A498 | >0.01 | >0.01 | >0.01 | 0.0038 | >0.01 | >0.01 | >0.01 |
| | Lung-NSC | NCI-H460 | 0.0079 | 0.009 | 0.0054 | 0.0011 | >0.01 | >0.01 | 0.0012 |
| | Colon | KM20L2 | >0.01 | >0.01 | 0.0012 | 0.0012 | >0.01 | >0.01 | 0.0012 |
| | Melanoma | SK-MEL-5 | >0.01 | >0.01 | 0.00074 | >0.01 | >0.01 | >0.01 | >0.01 |
| LC-50 (μg/ml) | Ovarian | OVCAR-3 | >0.01 | >0.01 | >0.01 | >0.01 | >0.01 | >0.01 | >0.01 |
| | CNS | SF-295 | >0.01 | >0.01 | >0.01 | >0.01 | >0.01 | >0.01 | >0.01 |
| | Renal | A498 | >0.01 | >0.01 | >0.01 | >0.01 | >0.01 | >0.01 | >0.01 |
| | Lung-NSC | NCI-H460 | >0.01 | >0.01 | >0.01 | >0.01 | >0.01 | >0.01 | >0.01 |
| | Colon | KM20L2 | >0.01 | >0.01 | >0.01 | >0.01 | >0.01 | >0.01 | >0.01 |
| | Melanoma | SK-MEL-5 | >0.01 | >0.01 | >0.01 | >0.01 | >0.01 | >0.01 | >0.01 |
| ED-50 (μg/ml) | Mouse Leukemia | PS-388 | 0.00256 | 0.000434 | 0.0000371 | 0.0000025 | 0.000839 | 0.00405 | 0.000271 |

TABLE 2

Human Cancer-Cell line and PS-388 Mouse Leukemia ($ED_{50}$) data for the tetrapeptide amides 10a–d

| | Cell type | Cell line | 10 a | 10 b | 10 c | 10 d |
|---|---|---|---|---|---|---|
| GI-50 (μg/ml) | Ovarian | OVCAR-3 | 0.000031 | 0.00031 | 0.0019 | 0.00029 |
| | CNS | SF-295 | 0.00027 | 0.00042 | 0.0035 | 0.0017 |
| | Renal | A498 | 0.00026 | 0.00069 | 0.0038 | 0.0059 |
| | Lung-NSC | NCI-H460 | 0.00022 | 0.00033 | 0.0029 | 0.0024 |
| | Colon | KM20L2 | 0.000034 | 0.00031 | 0.0020 | 0.00011 |
| | Melanoma | SK-MEL-5 | 0.000058 | 0.00043 | 0.0025 | 0.00091 |
| TGI (μg/ml) | Ovarian | OVCAR-3 | 0.00051 | 0.0012 | >0.01 | 0.012 |
| | CNS | SF-295 | >0.01 | >0.01 | >0.01 | 0.1 |
| | Renal | A498 | 0.0063 | >0.01 | >0.01 | 0.29 |
| | Lung-NSC | NCI-H460 | 0.0007 | 0.0014 | 0.0084 | 0.0097 |
| | Colon | KM20L2 | 0.001 | 0.0013 | >0.01 | 0.011 |
| | Melanoma | SK-MEL-5 | >0.01 | >0.01 | >0.01 | >1 |
| LC-50 (μg/ml) | Ovarian | OVCAR-3 | >0.01 | >0.01 | >0.01 | >1 |
| | CNS | SF-295 | >0.01 | >0.01 | >0.01 | >1 |
| | Renal | A498 | >0.01 | >0.01 | >0.01 | >1 |
| | Lung-NSC | NCI-H460 | >0.01 | >0.01 | >0.01 | >1 |
| | Colon | KM20L2 | >0.01 | >0.01 | >0.01 | >1 |
| | Melanoma | SK-MEL-5 | >0.01 | >0.01 | >0.01 | >1 |
| ED-50 (μg/ml) | Mouse Leukemia | PS-388 | 0.0000312 | 0.000357 | 0.00314 | 0.00586 |

The compound identified by reference (3) N—Z—Leu—Dil—OBu$^t$ was prepared in the following manner, following what is identified below as General Procedure A.

General Procedure A

To a solution of the hydrochloride salt of Dolaisoleuine t-butyl ester(2, 4.39 mM) and N—Z—(L)—Leucine (1, 4.83 mM) in dry dichloromethane (15 mL), cooled to ice-bath temperature (0°–5° C.) was added diisopropylethylamine (14.49 mM) followed by BrOP (4.83 mM) and the resulting solution was stirred at the same temperature for 2 hours. The solvents were removed under reduced pressure and the and 1101 cm$^{-1}$; $^1$H NMR(CDCl$_3$, 300 MHz): 7.32(m, 5H, ArH), 5.47 (d, J=8.9 Hz, 1H, NH), 5.08(s, 2H, ArCH$_2$), 4.68(m, 1H, dil N—CH), 4.55(m, 1H, Leu C$^\alpha$ H), 3.87(m, 1H, CH—OMe), 3.32(s, 3H, OMe), 2.92 (s, 3H, N—Me), 2.26–2.46 (m, 2H, CH$_2$CO), 1.30–1.70 (m, 6H, 2 x CH$_2$, 2 x CH), 1.44, 1.43(s, 9H, t—Bu) and 0.80–1.04(m, 12H, 4 x CH$_3$); EIMS (m/z): 506(M$^+$), 348, 279, 220, 177, 128, 100(100%) and 91.

The compound identified by reference (5) Dov—Leu—Dil—OBu$^t$ was prepared in the following manner, following what is identified below as General Procedure B.

General Procedure B

A solution of Z—Leu—Dil—OBu$^t$ (3, 2.22 mM) was dissolved in anhydrous methanol (10 mL) and cyclohexene (10 mL) was added in a nitrogen atmosphere. To the solution was added 5% Pd—C (1.15 g) and the mixture was heated at reflux for 6 minutes. The catalyst was removed by filtering through a layer of celite, the solvent removed under reduced pressure, and the residue dried in high vacuum for 2 hours.

To a solution of the above free base and N,N-dimethyl-(L)-valine( 4, 2.66 mM) in dry dichloromethane (10 mL) was added triethylamine (2.66 mM) followed by DECP (2.66 mM) at 0°–5° C. under argon atmosphere. After stirring at the same temperature for 2 hours, the solvent was removed and the residue chromatographed on a SILICA GEL column with 15% acetone in hexane as solvent to give the required tripeptide t-butyl ester as a colorless gummy mass (5, 65%); R$_f$ 0.69 (30% acetone-hexane); $[\alpha]_D^{25}$ –24.8° (c 5.0, CH$_3$OH); IR(neat): 2961, 1730, 1626, 1524, 1452, 1368, 1294, 1154 and 1101 cm$^{-1}$; $^1$H NMR(CDCl$_3$, 300 MHz): 6.82(br d, J=8.8 Hz, 1H, NH), 5.01(m, 1H, dil CHN), 4.60(br m, 1H, Leu C$^\alpha$—H), 3.85(m, 1H, CH—OMe), 3.33(s, 3H, OMe), 2.97(s, 3H, dil N—Me), 2.2–2.5(m, 2H, CH$_2$—CO), 2.24(s, 6H, NMe$_2$), 2.05(m, 1H, dov C$^\alpha$—H), 1.2–1.8(m, 7H, 2x CH$_2$, 3 x CH), 1.42, 1.44(s, 9H, t—Bu) and 0.75–0.99(m, 18H, 6 x CH$_3$); EIMS (m/z): 499(M$^+$), 456, 241, 186, 101, and 100(100%).

The tripeptide trifluoroacetate salt, identified above by reference (6) was synthesized following what is identified below as General Procedure C.

General Procedure C

To a solution of the tripeptide t-butyl ester (5, 10 mM) in dichloromethane (10 mL) cooled to ice-bath temperature was added trifluoroacetic acid (10 mL) under argon atmosphere and the solution was stirred at the same temperature for 1 hour. The solvents were then removed under reduced pressure, the residue was dissolved in toluene and solvent again removed under reduced pressure. The residue was dried in vacuo and crystallized from diethyl ether to obtain the tripeptide trifluoroacetate salt (6, quantitative) as a colorless solid; M.p. 168°–169° C.; $[\alpha]_D^{25}$ –36° (c 0.1, CHCl$_3$); IR (thin film): 2938, 2880, 2834, 1672, 1632, 1549, 1485, 1466, 1416, 1385, 1317, 1296, 1240, 1201, 1181, 1136, 1099, 1009, 990, 833, 799, 737, 721 and 617 cm$^{-1}$.

The pentapeptide amides herein identified by references 8a–g and 10a–d, were synthesized following General Procedure D shown below;

General Procedure D

To a solution of the trifluoroacetate salt (7a–g, 9a–d, 0.2 mM) in methylene chloride (2 mL, distilled from calcium hydride) was added the Dov—Leu—Dil tripeptide trifluoroacetate salt (6, 0.2 mM) followed by triethylamine (0.63 mM) and DECP (0.22 mM, ice bath). The solution was stirred under argon at 0°–5° C. for 1–2 hours. The solvent was removed (under vacuum at room temperature) and the residue was chromatographed on a SILICA GEL (0.040–0.063 mm) column. After the evaporation of solvent from the fractions (selected by thin layer chromatography) the required peptide amides were obtained as a fluffy solid.

Chromatography over SILICA GEL with hexane-acetone (2:3) as eluent, according to General Procedure D, yielded L-Dolavalyl-L-Leucyl-N-methyl-( 3R,4S,5S)-Dolaisoleuinyl-(2R,3R,4S)-Dolaproinyl-L-Methionine N-2-chlorophenylamide (8a) as a white solid (C$_{43}$H$_{73}$N$_6$O$_7$S$_1$Cl$_1$, 81%); Rf 0.26 (hexane-acetone 1:1); M.p. 88°–90° C., $[\alpha]_D^{23}$=–57.6° (c 0.17, CHCl$_3$); IR (thin film): 3293, 2963, 2932, 2876, 1628, 1593, 1532, 1441, 1385, 1370, 1294, 1269, 1233, 1200, 1165, 1134, 1099, 1051 and 752 cm$^{-1}$; EIMS (70 eV) m/z: 852 (M$^+$).

Chromatography over SILICA GEL with hexane-acetone (1:1) as eluent, according to General Procedure D, yielded L-Dolavalyl-L-Leucyl-N-methyl-( 3R,4S,5S)-Dolaisoleuinyl-(2R,3R,4S)-Dolaproinyl-L-Methionine N- 4-chlorophenylamide (8b) (C$_{43}$H$_{73}$N$_6$O$_7$S$_1$Cl$_1$, 98%); Rf 0.32 (hexane-acetone 1:1); M.p. 95°–96° C.; $[\alpha]_D^{23}$=–64.4° (c 0.09, CHCl$_3$); IR (thin film): 3306, 3293, 2961, 2934, 2874, 1643, 1626, 1543, 1493, 1449, 1418, 1404, 1385, 1368, 1304, 1289, 1269, 1250, 1198, 1169, 1134, 1098, 1038 and 829 cm$^{-1}$; EIMS (70 eV) m/z: 852 (M$^+$).

Chromatography over SILICA GEL with hexane-acetone (1:1) as eluent, according to General Procedure D, yielded L-Dolavalyl-L-Leucyl-N-methyl-( 3R,4S,5S)-Dolaisoleuinyl-(2R,3R,4S)-Dolaproinyl-L-Phenylalanine N-3-chlorophenylamide (8c) (C$_{47}$H$_{73}$N$_6$O$_7$Cl$_1$, 99%); Rf 0.34 (hexane-acetone 1:3); M.p. 86°–88 ° C.; $[\alpha]_D^{23}$ =–47.8° (C 0.18, CHCl$_3$); IR (thin film): 3306, 3293, 2963, 2934, 2876, 2832, 1649, 1626, 1595, 1545, 1483, 1452, 1425, 1385, 1368, 1302, 1267, 1250, 1236, 1194, 1167, 1134, 1099, 1038, 978, 779 and 741 cm$^{-1}$; EIMS (70 eV) m/z: 868 (M$^+$).

Chromatography over SILICA GEL with hexane-acetone (2:3) as eluent, according to General Procedure D, yielded L-Dolavalyl-L-Leucyl-N-methyl-( 3R,4S,5S)-Dolaisoleuinyl-(2R,3R,4S)-Dolaproinyl-L-Phenylalanine N-4-chlorophenylamide (8d) as a glassy solid (C$_{47}$H$_{73}$N$_6$O$_7$Cl$_1$, 82%); Rf 0.33 (hexane-acetone 1:1); M. p. 88°–90 ° C.; $[\alpha]_D^{23}$=–54.3° (c 0.14, CHCl$_3$); IR (thin film): 3306, 3295, 2961, 2932, 2874, 1649, 1626, 1543, 1493, 1454, 1418, 1404, 1385, 1368, 1306, 1290, 1269, 1248, 1200, 1134, 1098, 1038, 1015 and 829 cm$^{-1}$; EIMS (70 eV) m/z: 868 (M$^+$).

Chromatography over SILICA GEL with acetone-hexane (3:2) as eluent, according to General Procedure D, yielded L-Dolavalyl-L-Leucyl-N-methyl-( 3R,4S,5S)-Dolaisoleuinyl-(2R,3R,4S)-Dolaproinyl-L-Methionine N-2-benzothiazolamide (8e) (C$_{44}$H$_{73}$N$_7$O$_7$S$_2$, 93%); Rf 0.27 (hexane-acetone 1:1); $[\alpha]_D^{25}$=–49.2° (c 0.13, CHCl$_3$); M.p. 90°–92° C.; IR (thin film): 3306, 3293, 3214, 3196, 2961, 2932, 2874, 1626, 1547, 1443, 1420, 1387, 1368, 1263, 1235, 1194, 1165, 1099, 1036 and 756 cm$^{-1}$; EIMS m/z: 875 (M$^+$).

Chromatography over SILICA GEL with acetone-hexane (3:1) as eluent, according to General Procedure D, yielded L-Dolavalyl-L-Leucyl-N-methyl-( 3R,4S,5S)-Dolaisoleuinyl-(2R,3R,4S)-Dolaproinyl-L-Proline N-2-benzothiazolamide (8f) (C$_{44}$H$_{71}$N$_7$O$_7$S, 60%); Rf 0.20 (hexane-acetone 1:1); $[\alpha]_D^{25}$=–39.1° (c 0.11, CHCl$_3$); M.p. 96°–99 ° C.; IR (thin film): 3306, 2961, 2932, 2876, 1703, 1626, 1549, 1443, 1385, 1263, 1169 and 1098 cm$^{-1}$; EIMS m/z: 842 (M$^+$).

Chromatography over SILICA GEL with acetone-hexane (3:1) as eluent, according to General Procedure D, yielded L-Dolavalyl-L-Leucyl-N-methyl-( 3R,4S,5S)-Dolaisoleuinyl-(2R,3R,4S)-Dolaproinyl-L-Methionine N-3-quinolinamide (8 g) as a glassy solid (C$_{46}$H$_{75}$N$_7$O$_7$S, 83%); Rf 0.14 (hexane-acetone 1:1); $[\alpha]_D^{25}$=–46.9° (c 0.16, CHCl$_3$); M.p. 118°–120° C.; IR (thin film) n: 3291, 2963, 2934, 2876, 1649, 1632, 1580, 1555, 1489, 1452, 1422, 1385, 1368, 1346, 1304, 1283, 1271, 1202, 1181, 1134, 1099, 1042, 785, 754, 719 and 615 cm$^{-1}$; EIMS m/z: 869 (M$^+$).

Chromatography over SILICA GEL with acetone-hexane (3:1) as eluent, according to General Procedure D, yielded Dolavalyl-L-Leucyl-N-methyl-( 3R,4S,5S)-Dolaisoleuinyl-(2R,3R,4S)-Dolaproinyl-Dolaphenine (10a) as a glassy solid ($C_{43}H_{70}N_6O_6S$, 84%); M.p. 77°–78 °C.; $R_f$ 0.2 (acetone-hexane 1:1); $[\alpha]_D^{25}$ –68.6° (c 0.14, $CHCl_3$); IR(thin film): 3295, 2960, 2934, 2876, 2830, 1624, 1535, 1497, 1454, 1418, 1385, 1370, 1319, 12287, 1267, 1225, 1200, 1171, 1136, 1101, 1040, 735, 698, 619, 610 and 536 $cm^{-1}$; EIMS (m/z): 798($M^+$).

Chromatography over SILICA GEL with acetone-hexane (3:1) as eluent, according to General Procedure D, yielded L-Dolavalyl-L-Leucyl-N-methyl-( 3R,4S,5S)-Dolaisoleuinyl-(2R,3R,4S)-Dolaproinyl-N- 2(2-chlorophenyl) ethylamide (10b) as a gummy mass ($C_{40}H_{68}N_5O_6Cl_1$, 77%); $R_f$ 0.27 (acetone-hexane 1:1); $[\alpha]_D^{25}$ –54.3° (c 0.07, $CHCl_3$); IR(thin film): 3308, 2961, 2934, 2876, 2830, 1624, 1537, 1451, 1418, 1383, 1366, 1287, 1269, 1223, 1198, 1169, 1157, 1134, 1101, 1055, 1040 and 754 $cm^{-1}$; EIMS (m/z): 749($M^+$).

Chromatography over SILICA GEL with acetone-hexane (3:1) as eluent, according to General Procedure D, yielded L-Dolavalyl-L-Leucyl-N-methyl-( 3R, 4S, 5S) -Dolaisoleuinyl- (2R, 3R, 4S) -Dolaproinyl-N- 2(3-chlorophenyl) ethylamide (10c) as a gummy mass ($C_{40}H_{68}N_5O_6Cl_1$, 75%); $R_f$ 0.23 (acetone-hexane 1:1); $[\alpha]_D^{25}$ –47.8° (c 0.09, $CHCl_3$); IR(thin film): 3308, 2961, 2934, 2876, 2830, 1643, 1624, 1537, 1452, 1418, 1383, 1366, 1289, 1267, 1223, 1200, 1169, 1136, 1101, 1039, 781 and 685 $cm^{-1}$; EIMS (m/z): 749($M^+$).

Chromatography over SILICA GEL with acetone-hexane (3:1) as eluent, according to General Procedure D, yielded L-Dolavalyl-L-Leucyl-N-methyl-( 3R,4S,5S)-Dolaisoleuinyl-(2R,3R,4S)-Dolaproinyl-N- 2(4-chlorophenyl) ethylamide (10d) as a glassy solid ($C_{40}H_{68}N_5O_6Cl_1$, 79%); $R_f$ 0.54 (acetone-hexane 3:1); M.p. 67°–70° C.; $[\alpha]_D^{25}$ –72.2° (c 0.09, $CHCl_3$); IR(thin film): 3308, 2961, 2934, 2876, 2830, 1624, 1541, 1493, 1451, 1418, 1385, 1366, 1269, 1225, 1198, 1136, 1099 and 1040 $cm^{-1}$; EIMS (m/z): 749($M^+$).

To further aid in the understanding of the present invention, and not by way of limitation the following examples are presented.

EXAMPLE I

N—Z—Leu—Dil—OBu'(3) was prepared as follows: To a solution of the hydrochloride salt of Dolaisoleuine t-butyl ester (2, 4.39 mM) and N—Z—(L)—Leucine (1, 4.83 mM) in dry dichloromethane (15 mL), cooled to ice-bath temperature (0°–5° C.) was added diisopropylethylamine (14.49 mM) followed by BrOP (4.83 mM) and the resulting solution was stirred at the same temperature for 2 hours. The solvents were removed under reduced pressure and the residue was chromatographed on a SILICA GEL column using 1:4 acetone-hexane as the solvent to obtain the required dipeptide as an oily substance (3, 72%); $R_f$ 0.53 (1:4 acetone-hexane); $[\alpha]_D^{25}$ –33.4° (c 6.2, $CH_3OH$); IR(neat): 2961, 1723, 1640, 1528, 1456, 1368, 1254, 1154 and 1101 $cm^{-1}$; $^1H$ NMR($CDCl_3$, 300 MHz): 7.32(m, 5H, ArH), 5.47 (d, J=8.9 Hz, 1H, NH), 5.08(s, 2H, $ArCH_2$), 4.68(m, 1H, dil N—CH), 4.55(m, 1H, Leu $C^\alpha$ H), 3.87(m, 1H, CH—OMe), 3.32(s, 3H, OMe), 2.92 (s, 3H, N—Me), 2.26–2.46 (m, 2H, $CH_2CO$), 1.30–1.70 (m, 6H, 2 x $CH_2$, 2 x CH), 1.44, 1.43(s, 9H, t—Bu) and 0.80–1.04(m, 12H, 4 x $CH_3$); EIMS (m/z): 506($M^+$), 348, 279, 220, 177, 128, 100(100%) and 91.

EXAMPLE II

Dov—Leu—Dil—OBu'(5) was prepared as follows: A solution of Z—Leu—Dil—OBu ' (3, 2.22 mM) was dissolved in anhydrous methanol (10 mL) and cyclohexene (10 mL) was added in a nitrogen atmosphere. To the solution was added 5% Pd—C (1.15 g) and the mixture was heated at reflux for 6 minutes. The catalyst was removed by filtering through a layer of celite, the solvent removed under reduced pressure, and the residue dried in high vacuum for 2 hours.

To a solution of the above free base and N,N-dimethyl-(L)-valine( 4, 2.66 mM) in dry dichloromethane (10 mL) was added triethylamine (2.66 mM) followed by DECP (2.66 mM) at 0°–5° C. under argon atmosphere. After stirring at the same temperature for 2 hours, the solvent was removed and the residue chromatographed on a SILICA GEL column with 15% acetone in hexane as solvent to give the required tripeptide t-butyl ester as a colorless gummy mass (5, 65%); $R_f$ 0 69 (30% acetone-hexane); $[\alpha]_D^{25}$ –24.8° (c 5.0, $CH_3OH$); IR(neat): 2961, 1730, 1626, 1524, 1452, 1368, 1294, 1154 and 1101 $cm^{-1}$; $^1H$ NMR($CDCl_3$, 300 MHz): 6.82(br d, J=8.8 Hz, 1H, NH), 5.01(m, 1H, dil CHN), 4.60(br m, 1H, Leu $C^\alpha$—H), 3.85(m, 1H, CH—OMe), 3.33(s, 3H, OMe), 2.97(s, 3H, dil N—Me), 2.2–2.5(m, 2H, $CH_2$—CO), 2.24 (s, 6H, $NMe_2$), 2.05 (m, 1H, dov $C^\alpha$—H), 1.2–1.8 (m, 7H, 2x $CH_2$, 3 x CH), 1.42, 1.44(s, 9H, t—Bu) and 0.75–0.99(m, 18H, 6 x $CH_3$); EIMS (m/z): 499($M^+$), 456, 241, 186, 101, and 100(100%).

EXAMPLE III

Tripeptide Trifluoroacetate Salt(6) was prepared as follows: To a solution of the tripeptide t-butyl ester(5, 10 mM) in dichloromethane(10 mL) cooled to ice-bath temperature was added trifluoroacetic acid(10 mL) under argon atmosphere and the solution was stirred at the same temperature for 1 hour. The solvents were then removed under reduced pressure, the residue was dissolved in toluene and solvent again removed under reduced pressure. The residue was dried in vacuo and crystallized from diethyl ether to obtain the tripeptide trifluoroacetate salt(6, quantitative) as a colorless solid; M.p. 168°–169° C.; $[\alpha]_D^{25}$ –36° (c 0.1, $CHCl_3$); IR(thin film): 2938, 2880, 2834, 1672, 1632, 1549, 1485, 1466, 1416, 1385, 1317, 1296, 1240, 1201, 1181, 1136, 1099, 1009, 990, 833, 799, 737, 721 and 617 $cm^{-1}$.

EXAMPLE IV

Pentapeptide amides 8a–g, 10a–d were prepared as follows: To a solution of the trifluoroacetate salt (7a–g, 9a–d, 0.2 mM) in methylene chloride (2 mL, distilled from calcium hydride) was added the Dov—Leu—Dil tripeptide trifluoroacetate salt (6, 0.2 mM) followed by triethylamine (0.63 mM) and DECP (0.22 mM, ice bath). The solution was stirred under argon at 0°–5° C. for 1–2 hours. The solvent was removed (under vacuum at room temperature) and the residue was chromatographed on a SILICA GEL (0.040–0.063 mm) column. After the evaporation of solvent from the fractions (selected by thin layer chromatography), the required peptide amides were obtained as a fluffy solid.

EXAMPLE IV-a

Chromatography over SILICA GEL with hexane-acetone (2:3) as eluent, according to General Procedure D, yielded L-Dolavalyl-L-Leucyl-N-methyl-( 3R,4S,5S)-Dolaisoleuinyl-(2R,3R,4S)-Dolaproinyl-L-Methionine N-2-chlorophenylamide (8a) as a white solid ($C_{43}H_{73}N_6O_7S_1Cl_1$, 81%); $R_f$ 0.26 (hexane-acetone 1:1); M.p. 88°–90 ° C., $[\alpha]_D^{23}$=–57.6° (c 0.17, $CHCl_3$); IR (thin film): 3293, 2963, 2932, 2876, 1628, 1593, 1532, 1441, 1385, 1370, 1294, 1269, 1233, 1200, 1165, 1134, 1099, 1051 and 752 cm$^{-1}$; EIMS (70 eV) m/z: 852 (M$^+$).

EXAMPLE IV-b

Chromatography over SILICA GEL with hexane-acetone (1:1) as eluent, according to General Procedure D, yielded L-Dolavalyl-L-Leucyl-N-methyl-(3R,4S,5S)-Dolaisoleuinyl-(2R,3R,4S)-Dolaproinyl-L-Methionine N-4-chlorophenylamide (8b) ($C_{43}H_{73}N_6O_7S_1Cl_1$, 98%); Rf 0.32 (hexane-acetone 1:1); M.p. 95°–96° C.; $[\alpha]_D^{23}=-64.4°$ (c 0.09, CHCl$_3$); IR (thin film): 3306, 3293, 2961, 2934, 2874, 1643, 1626, 1543, 1493, 1449, 1418, 1404, 1385, 1368, 1304, 1289, 1269, 1250, 1198, 1169, 1134, 1098, 1038 and 829 cm$^{-1}$; EIMS (70 eV) m/z: 852 (M$^+$).

EXAMPLE IV-c

Chromatography over SILICA GEL with hexane-acetone (1:1) as eluent, according to General Procedure D, yielded L-Dolavalyl-L-Leucyl-N-methyl-(3R,4S,5S)-Dolaisoleuinyl-(2R,3R,4S)-Dolaproinyl-L-Phenylalanine N-3-chlorophenylamide (8c) ($C_{47}H_{73}N_6O_7Cl_1$, 99%); Rf 0.34 (hexane-acetone 1:3); M.p. 86°–88° C.; $[\alpha]_D^{23}=-47.8°$ (c 0.18, CHCl$_3$); IR (thin film): 3306, 3293, 2963, 2934, 2876, 2832, 1649, 1626, 1595, 1545, 1483, 1452, 1425, 1385, 1368, 1302, 1267, 1250, 1236, 1194, 1167, 1134, 1099, 1038, 978, 779 and 741 cm$^{-1}$; EIMS (70 eV) m/z: 868 (M$^+$).

EXAMPLE IV-d

Chromatography over SILICA GEL with hexane-acetone (2:3) as eluent, according to General Procedure D, yielded L-Dolavalyl-L-Leucyl-N-methyl-(3R,4S,5S)-Dolaisoleuinyl-(2R,3R,4S)-Dolaproinyl-L-Phenylalanine N-4-chlorophenylamide (8d) as a glassy solid ($C_{47}H_{73}N_6O_7Cl_1$, 82%); Rf 0.33 (hexane-acetone 1:1); M.p. 88°–90° C.; $[\alpha]_D^{23}=-54.3°$ (c 0.14, CHCl$_3$); IR (thin film) n: 3306, 3295, 2961, 2932, 2874, 1649, 1626, 1543, 1493, 1454, 1418, 1404, 1385, 1368, 1306, 1290, 1269, 1248, 1200, 1134, 1098, 1038, 1015 and 829 cm$^{-1}$; EIMS (70 eV) m/z: 868 (M$^+$).

EXAMPLE IV-e

Chromatography over SILICA GEL with acetone-hexane (3:2) as eluent according to General Procedure D, yielded L-Dolavalyl-L-Leucyl-N-methyl-(3R,4S,5S)-Dolaisoleuinyl-(2R,3R,4S)-Dolaproinyl-L-Methionine N-2-benzothiazolamide (8e) ($C_{44}H_{73}N_7O_7S_2$, 93%); Rf 0.27 (hexane-acetone 1:1); $[\alpha]_D^{25}=-49.2°$ (c 0.13, CHCl$_3$); M.p. 90°–92° C.; IR (thin film): 3306, 3293, 3214, 3196, 2961, 2932, 2874, 1626, 1547, 1443, 1420, 1387, 1368, 1263, 1235, 1194, 1165, 1099, 1036 and 756 cm$^{-1}$; EIMS m/z: 875 (M$^+$).

EXAMPLE IV-f

Chromatography over SILICA GEL with acetone-hexane (3:1) as eluent, according to General Procedure D, yielded L-Dolavalyl-L-Leucyl-N-methyl-(3R,4S,5S)-Dolaisoleuinyl-(2R,3R,4S)-Dolaproinyl-L-Proline N-2-benzothiazolamide (8f) ($C_{44}H_{71}N_7O_7S$, 60%); Rf 0.20 (hexane-acetone 1:1); $[\alpha]_D^{25}=-39.1°$ (c 0.11, CHCl$_3$); M.p. 96°–99° C.; IR (thin film): 3306, 2961, 2932, 2876, 1703, 1626, 1549, 1443, 1385, 1263, 1169 and 1098 cm$^{-1}$; EIMS m/z: 842 (M$^+$).

EXAMPLE IV-g

Chromatography over SILICA GEL with acetone-hexane (3:1) as eluent according to General Procedure D, yielded L-Dolavalyl-L-Leucyl-N-methyl-(3R,4S,5S)-Dolaisoleuinyl-(2R,3R,4S)-Dolaproinyl-L-Methionine N-3-quinolinamide (8 g) as a glassy solid ($C_{46}H_{75}N_7O_7S$, 83%); Rf 0.14 (hexane-acetone 1:1); $[\alpha]_D^{25}=-46.9°$ (c 0.16, CHCl$_3$); M. p. 118°–120° C.; IR (thin film): 3291, 2963, 2934, 2876, 1649, 1632, 1580, 1555, 1489, 1452, 1422, 1385, 1368, 1346, 1304, 1283, 1271, 1202, 1181, 1134, 1099, 1042, 785, 754, 719 and 615 cm$^{-1}$; EIMS m/z: 869 (M$^+$).

EXAMPLE V-a

Chromatography over SILICA GEL with acetone-hexane (3:1) as eluent, according to General Procedure D, yielded L-Dolavalyl-L-Leucyl-N-methyl-(3R,4S,5S)-Dolaisoleuinyl-(2R,3R,4S)-Dolaproinyl-Dolaphenine (10a) as a glassy solid ($C_{43}H_{70}N_6O_6S$, 84%); M.p. 77°–78 ° C.; R$_f$ 0.2 (acetone-hexane 1:1); $[\alpha]_D^{25}$ −68.6° (c 0.14, CHCl$_3$); IR(thin film): 3295, 2960, 2934, 2876, 2830, 1624, 1535, 1497, 1454, 1418, 1385, 1370, 1319, 12287, 1267, 1225, 1200, 1171, 1136, 1101, 1040, 735, and 698 cm$^{-1}$; EIMS (m/z): 798(M$^+$).

EXAMPLE V-b

Chromatography over SILICA GEL with acetone-hexane (3:1) as eluent according to General Procedure D, yielded L-Dolavalyl-L-Leucyl-N-methyl-(3R,4S,5S)-Dolaisoleuinyl-(2R,3R,4S)-Dolaproinyl-N-2(2-chlorophenyl) ethylamide (10b) as a gummy mass ($C_{40}H_{68}N_5O_6Cl_1$, 77%); R$_f$ 0.27 (acetone-hexane 1:1); $[\alpha]_D^{25}$ −54.3° (c 0.07, CHCl$_3$); IR(thin film): 3308, 2961, 2934, 2876, 2830, 1624, 1537, 1451, 1418, 1383, 1366, 1287, 1269, 1223, 1198, 1169, 1157, 1134, 1101, 1055, 1040 and 754 cm$^{-1}$; EIMS (m/z): 749(M$^+$).

EXAMPLE V-c

Chromatography over SILICA GEL with acetone-hexane (3:1) as eluent, according to General Procedure D, yielded L-Dolavalyl-L-Leucyl-N-methyl-(3R,4S,5S)-Dolaisoleuinyl-(2R,3R,4S)-Dolaproinyl-N-2(3-chlorophenyl) ethylamide (10c) as a gummy mass ($C_{40}H_{68}N_5O_6Cl_1$, 75%); R$_f$ 0.23 (acetone-hexane 1:1); $[\alpha]_D^{25}$ −47.8° (c 0.09, CHCl$_3$); IR(thin film): 3308, 2961, 2934, 2876, 2830, 1643, 1624, 1537, 1452, 1418, 1383, 1366, 1289, 1267, 1223, 1200, 1169, 1136, 1101, 1039, 781 and 685 cm$^{-1}$; EIMS (m/z): 749(M$^+$).

EXAMPLE V-d

Chromatography over SILICA GEL with acetone-hexane (3:1) as eluent, according to General Procedure D, yielded L-Dolavalyl-L-Leucyl-N-methyl-(3R,4S,5S)-Dolaisoleuinyl-(2R,3R,4S)-Dolaproinyl-N-2(4-chlorophenyl) ethylamide (10d) as a glassy solid ($C_{40}H_{68}N_5O_6Cl_1$, 79%); R$_f$ 0.54 (acetone-hexane 3:1); M.p. 67°–70 ° C.; $[\alpha]_D^{25}$ −72.2° (c 0.09, CHCl$_3$); IR(thin film): 3308, 2961, 2934, 2876, 1624, 1541, 1493, 1451, 1418, 1385, 1366, 1269, 1225, 1198, 1136, 1099 and 1040 cm$^{-1}$; EIMS (m/z): 749(M$^+$).

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A substantially pure compound having the general structure below:

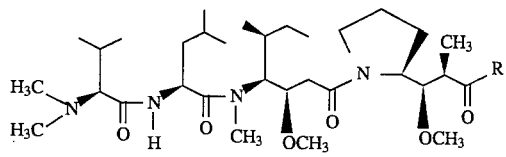

wherein R is selected from the group consisting of: Met—NH—2ClPh, "8a"; Met—NH—4ClPh, "8b"; Phe—NH—3ClPh, "8c"; Phe—NH—4ClPh, "8d"; Met—NH—BnThz, "8e"; Pro—NH—BnThz, "8f"; and Met—NH—Q, "8g".

2. A substantially pure compound according to claim 1 wherein R=Met—NH—2ClPh.

3. A substantially pure compound according to claim 1 wherein R=Met—NH—4ClPh.

4. A substantially pure compound according to claim 1 wherein R=Phe—NH—3ClPh.

5. A substantially pure compound according to claim 1 wherein R=Phe—NH—4ClPh.

6. A substantially pure compound according to claim 1 wherein R=Met—NH—BnThz.

7. A substantially pure compound according to claim 1 wherein R=Pro—NH—BnThz.

8. A substantially pure compound according to claim 1 wherein R=Met—NH—Q.

* * * * *